United States Patent [19]
Prather

[11] Patent Number: 5,498,250
[45] Date of Patent: Mar. 12, 1996

[54] CATHETER GUIDE WIRE WITH MULTIPLE RADIOPACITY

[75] Inventor: Richard R. Prather, Rogers, Minn.

[73] Assignee: SciMed Life Systems, Inc., Maple Grove, Minn.

[21] Appl. No.: 245,339

[22] Filed: May 18, 1994

[51] Int. Cl.⁶ .................................................. A61B 5/00
[52] U.S. Cl. ............................................................ 604/280
[58] Field of Search .................................. 128/656, 657, 128/772; 604/280, 95, 164, 281–285

[56] References Cited

U.S. PATENT DOCUMENTS

| | | | |
|---|---|---|---|
| 3,789,841 | 2/1974 | Antoshkiw | 128/2.05 |
| 4,538,622 | 9/1985 | Samson et al. | 128/772 |
| 4,545,390 | 10/1985 | Leary | 128/772 |
| 4,619,274 | 10/1986 | Morrison | 128/772 |
| 4,763,647 | 8/1988 | Gambale | 128/657 |
| 4,798,598 | 1/1989 | Bonello et al. | 128/772 |
| 4,830,023 | 5/1989 | de Toledo et al. | 128/772 |
| 4,846,186 | 7/1989 | Box et al. | 128/657 |
| 4,884,579 | 12/1989 | Engelson | 128/772 |
| 4,922,924 | 5/1990 | Gambale et al. | 128/772 |
| 4,934,380 | 6/1990 | de Toledo | 128/772 |
| 4,953,553 | 9/1990 | Tremulis | 128/772 |
| 5,063,935 | 11/1991 | Gambale | 128/657 |
| 5,084,022 | 1/1992 | Claude | 128/772 |
| 5,144,959 | 9/1992 | Gambale et al. | 128/772 |
| 5,147,317 | 9/1992 | Shank et al. | 604/164 |
| 5,174,302 | 12/1992 | Palmer | 128/772 |
| 5,201,754 | 4/1993 | Crittenden et al. | 606/194 |
| 5,213,111 | 5/1993 | Cook et al. | 128/772 |
| 5,228,453 | 7/1993 | Sepetka | 128/772 |
| 5,234,003 | 8/1993 | Hall | 128/772 |
| 5,253,653 | 10/1993 | Daigle et al. | 128/772 |
| 5,259,393 | 11/1993 | Corso, Jr. et al. | 128/772 |
| 5,267,574 | 12/1993 | Viera et al. | 128/772 |

FOREIGN PATENT DOCUMENTS

WO93/08862  5/1993  WIPO.

Primary Examiner—C. Fred Rosenbaum
Assistant Examiner—Manuel Mendez
Attorney, Agent, or Firm—Nawrocki, Rooney & Sivertson

[57] ABSTRACT

An apparatus and method for a thin, flexible catheter guide wire having portions of uniform and tapering diameters, a helical coil of a first radiopacity encasing or covering the distal end of the wire, and at least one additional wire cover of a lubricous material which is formed to be radiopaque but which has a radiopacity different than that of the helical coil. This improved device enables the use of an improved method of placement with the use of fluoroscopy to steer and locate the guide wire, and thus the catheter ultimately placed over the guide wire, at a precise situs within the body.

15 Claims, 3 Drawing Sheets

CATHETER GUIDE WIRE WITH MULTIPLE RADIOPACITY

BACKGROUND OF THE INVENTION

1. Field of the Invention

The present invention relates in general to medical instrumentation, and more particularly to intraluminal devices, and still more particularly to guide wires for intraluminal devices including catheters.

2. Description of the Prior Art

The use of intraluminal catheters for treatment of various medical problems within the body is well known. It is also well known that a variety of problems are encountered as the catheter is steered through the selected lumen to a desired point in the body. The path may be tortuous and the point of interest may be difficult to locate precisely. A continuing series of technical improvements and additions have been made in the catheter field to provide devices and methods which can overcome certain of the difficulties. One such series of improvements has resulted in the now well known use of a thin flexible guide wire which includes a radiopaque tip or distal portion and which can be more easily steered through the lumen and which can be more precisely placed with the use of a fluoroscope to read the location of the tip. A desired catheter can then be slid over the guide wire to reached the desired situs in the body.

U.S. Pat. No. 3,789,841, for example, teaches the use of a guide wire having portions of uniform diameter adjacent to portions of tapered diameter to provide increase flexibility. The teaching includes encasing the distal end of the guide wire in a coiled spring and the remainder of the wire in a Teflon jacket.

U.S. Pat. No. 4,545,390, for example, also teaches the use of a thin guide wire having both uniform and tapered diameter portions and having a helically wound spring encasing a tapered portion at its distal end. In this teaching, at least part of the spring is formed from a material having a high degree of radiopacity for the purpose of fluoroscopic observation.

U.S. Pat. No. 4,884,579, for example, teaches yet another version of the above described thin, flexible guide wire that has a portion encased in a lubricous material such as Teflon to facilitate the passage of a catheter over the wire after it has been situated in the body.

U.S. Pat. No. 5,201,754 teaches the use of varying radiopacity in an angioplasty balloon catheter to better enable its steerage through a body lumen.

SUMMARY OF THE INVENTION

The present invention adds to the improvements of the prior art by providing a thin, flexible catheter guide wire having portions of uniform and tapering diameters, a helical coil of a first radiopacity encasing or covering the distal end of the wire, and at least one additional wire cover of a lubricous material which is formed to be radiopaque but which has a radiopacity different than that of the helical coil. This improved device enables the use of an improved method of placement with the use of fluoroscopy to steer and locate the guide wire, and thus the catheter ultimately placed over the guide wire, at a precise situs within the body.

BRIEF DESCRIPTION OF THE DRAWINGS

The objects and many of the attendant advantages of the present invention will be readily appreciated as it becomes better understood by reference to the following detailed description when considered in connection with the accompanying drawings, in which like reference numerals designate like parts throughout the figures thereof and wherein.

DETAILED DESCRIPTION OF THE PREFERRED EMBODIMENTS

Figure 1:
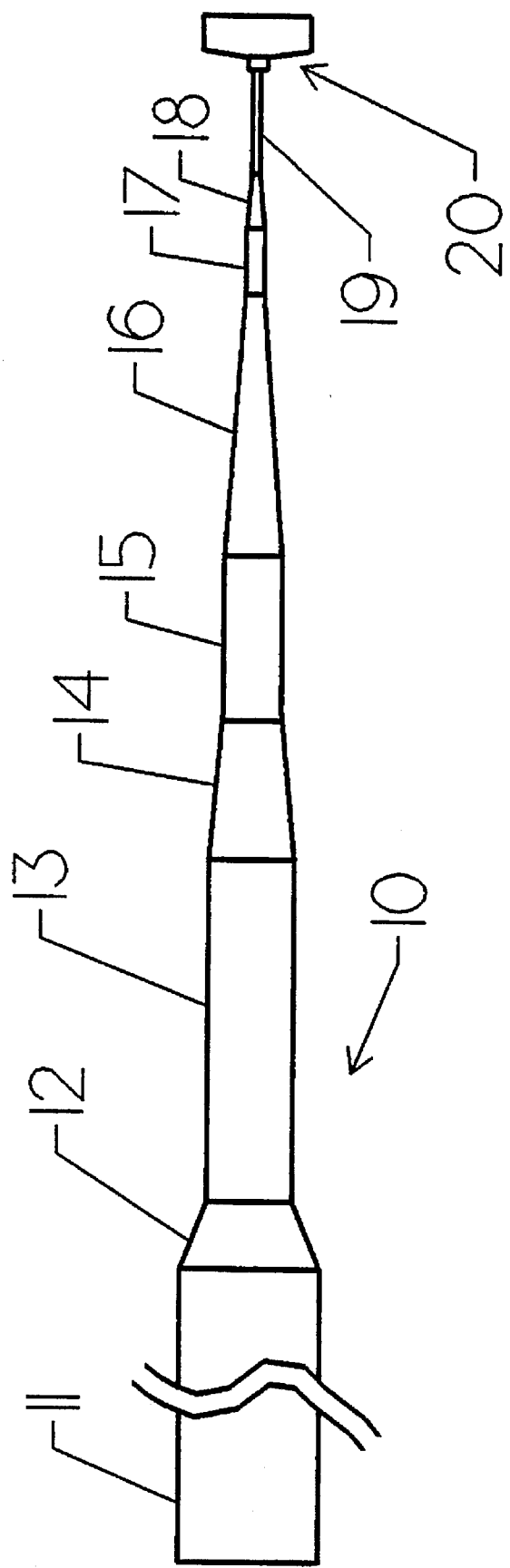
FIG. 1 is a plan view showing a thin, flexible wire having alternating portions of uniform and tapering diameters, and representing the preferred guide wire of this invention.

FIG. 1 discloses a catheter guide wire indicated generally at 10. Wire 10 has a plurality of steps of uniform diameters 11, 13, 15 and 17, alternately interspersed with a plurality of steps of tapering diameter 12, 14, 16 and 18. The use of steps such as 11–19 is known in the art for the purpose of adding flexibility and ease of steerage to the guide wire. Step 11 is at the proximal end of wire 10, where the steering is initiated, while step 19 is at the distal end of wire 10 where the greatest flexibility is desired. As shown in FIG. 1, step 19 is connected at its distal end to a tip construction component indicated at 20. Construction component 20 is adapted to be utilized in a tip member such as a ball-tip to protect the lumen walls as guide wire 10 is passed therethrough to reach its destination within the body.

Figure 2:
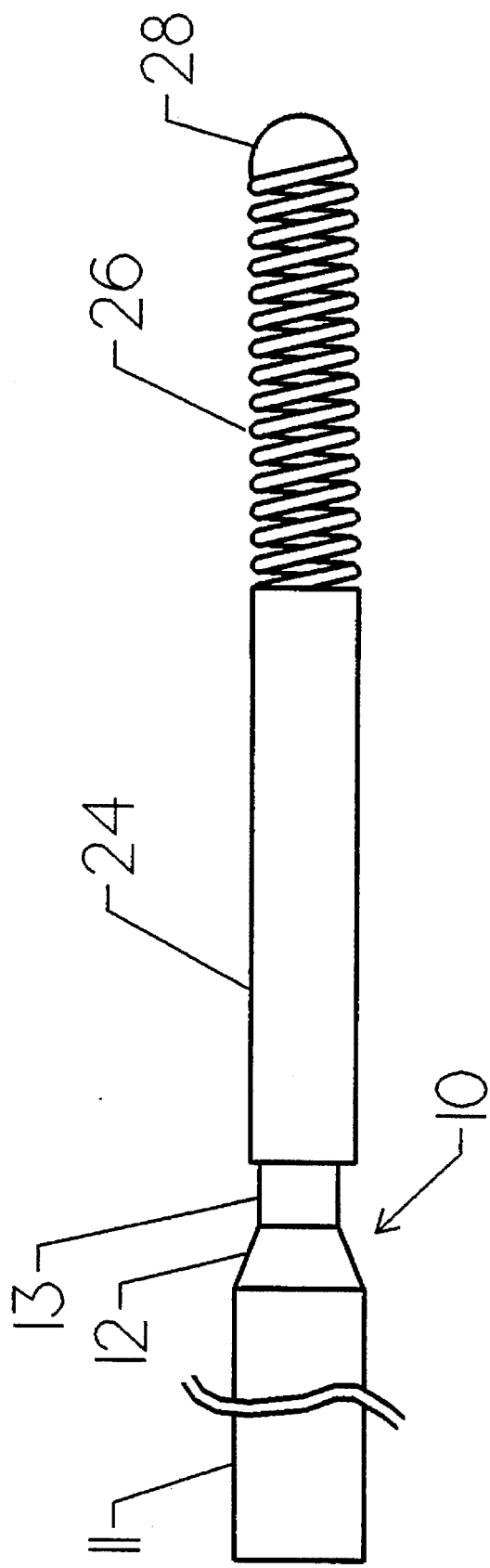
FIG. 2 is a plan view of one preferred embodiment of the invention showing a helical coil and a lubricous member covering a portion of the wire of FIG. 1.

FIG. 2 discloses a tip member 28 which has been formed with tip construction component 20 (not shown in FIG. 2). Also shown is a helical coil 26 which is mounted over wire 10 and extends proximately from member 28. For purposes of clarity, any portion of wire 10 which might be visible within coil 26 has been omitted from FIG. 2, but reference to FIG. 1 will make clear the portion of wire 10 that is covered by coil 26. Coil 26 is flexible and at least a portion of coil 26 is made of a material, such as that having a first radiopacity, in a manner known to those familiar with the prior art.

FIG. 2 also discloses a wire covering member 24, shown here as a sleeve, which is mounted on wire 10 and extends proximately from coil 26 to cover a selected portion of wire 10. According to the present invention, member 24 is preferably a lubricous polymer which has been properly loaded to have a radiopacity different from that of coil 26. It is this second level of radiopacity, preferably but not by way of limitation of a lower level than that of coil 26, which provides the improved method of steering the guide wire 10 through the lumens of the body by enabling the operator to have additional fluoroscopic information. In the preferred embodiment of FIG. 2, wire covering 24 comprises a Pebax polymer sleeve which has been loaded with a mixture that includes barium sulfate or other barium salts to provide the desired radiopacity. In the preferred embodiment the mixture comprises 60% to 70% barium sulfate. Reference is made to U.S. Pat. No. 5,245,195 regarding x-ray attenuation provided by a film of thermoplastic elastomer containing barium sulfate. It is also recognized that bismuth, tungsten, platinum and other high molecular weight metals may also be used for polymer loading 30%–80% by weight.

Figure 3:
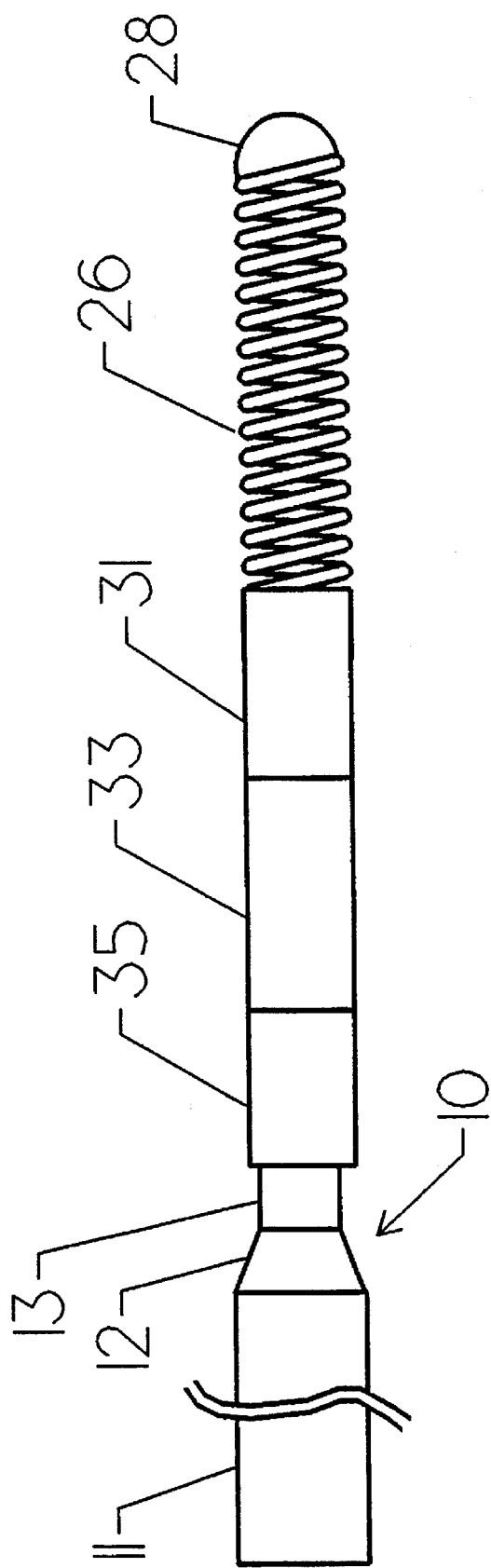
FIG. 3 is a plan view of a second preferred embodiment of this invention in which a plurality of lubricous wire covers are used.

FIG. 3 discloses another preferred embodiment of the guide wire of this invention which comprises a device similar to that of FIG. 2 except that covering member 24 of FIG. 2 has been replaced with a series of wire covering members 31, 33 and 35. Each of members 31, 33 and 35 is made of a polymer loaded to have a radiopacity different from one another and different from the radiopacity of coil 26. This plurality of radiopacity signals seen on a fluoroscope will provide still further information to the operator of the placement of guide wire 10, thus enhancing the opportunity for more precise placement.

It is recognized that the loading of the polymer for radiopacity can also be done using a mixture of several high molecular weight metals and metal salts. It has been found that doing so creates greater radiopacity than could be achieved using a single component loading of equal amount. One preferred embodiment is a blend of barium sulfate, bismuth oxychloride and tungsten. The resulting blend can then be loaded into the polymer 20–80% by weight to achieve the desired radiopacity.

Having thus described the preferred embodiments of the present invention, those of skill in the art will readily appreciate the other useful embodiments within the scope of the attached claims.

I claim:

1. In a guide wire apparatus having a length of flexible wire with proximal and distal ends, a tip at the distal end of the guide wire, a first wire covering adjacent the tip and having a first radiopacity, and further wire coverings including at least a second wire covering placed intermediate the first wire covering and the proximal end of the guide wire, the improvement comprising:

a. the second wire covering including a sleeve, the sleeve including a mixture of a polymer and a radiopaque metal loading the second wire covering having a second radiopacity; and b. the second radiopacity being unequal to the first radiopacity.

2. The improved apparatus of claim 1 in which the second radiopacity is less than the first radiopacity.

3. The improved apparatus of claim 1 in which the second radiopacity is greater than the first radiopacity.

4. The improved apparatus of claim 1 in which the further wire coverings each have a radiopacity different from the first radiopacity.

5. The improved apparatus of claim 4 in which the radiopacity of each of the further wire coverings differs from every other wire covering radiopacity.

6. The apparatus of claims 1, 2 or 3 in which the polymer sleeve of the second wire covering has a load mixture of a radiopaque metal selected from the group consisting of bismuth, tungsten, platinum or barium sulfate.

7. The apparatus of claim 6 in which the load mixture is in the range of 60–70%.

8. The apparatus of claims 1, 4 or 5 in which the further wire coverings comprise polymer sleeves mounted to the guide wire and made of a material including a load of a mixture of a radiopaque metal.

9. The apparatus of claim 8 in which the load mixture is in the range of 60–70%.

10. The improved method of fluoroscopic placement of a catheter guide wire comprising the steps of:

a. mounting a first wire covering adjacent a distal end of the guide wire;

b. mounting at least a second wire covering intermediate the first covering and a proximal end of the guide wire, the second wire covering including a sleeve, the sleeve including a mixture of a polymer and a radiopaque metal loading.

c. providing the first wire covering with a first radiopacity; and d. providing the second wire covering with a second radiopacity different than the first radiopacity.

11. The improved method of fluoroscopic placement of a catheter guide wire comprising the steps of:

a. mounting a first wire covering adjacent a distal end of the guide wire;

b. mounting a plurality of further wire coverings intermediate the first covering and a proximal end of the guide wire, each further wire covering including a sleeve, the sleeve including a mixture of a polymer and a radiopaque metal loading;

c. providing the first wire covering with a first radiopacity;

d. providing each of the further wire coverings with a different radiopacity; and e. making each of the different radiopacities different than the first radiopacity.

12. Catheter guide wire apparatus comprising:

a. a length of flexible wire having proximal and distal ends;

b. a tip connected to the distal end of the wire;

c. a flexible coil mounted around the wire adjacent to the tip and extending proximately therefrom;

d. a first polymer sleeve, the sleeve including a mixture of a polymer and a radiopaque metal loading, mounted around the wire adjacent to the coil and extending proximately therefrom;

e. at least a portion of the coil having a first radiopacity; and f. at least a portion of the polymer sleeve having a second radiopacity different than the first radiopacity.

13. The apparatus of claim 12 including:

a. further polymer sleeves mounted around the wire intermediate the first polymer sleeve and the proximal end of the wire; and b. the further polymer sleeves each having a radiopacity different from one another and different from the coil and first polymer sleeve radiopacities.

14. The apparatus of claims 12 or 13 in which the first and further polymer sleeves comprise a lubricous polymer material.

15. The apparatus of claim 14 in which the polymer material is loaded with a mixture selected from the group consisting of barium sulfate, bismuth, tungsten, or platinum.

* * * * *